United States Patent [19]

Yamamoto

[11] Patent Number: 5,007,116
[45] Date of Patent: Apr. 16, 1991

[54] PORTABLE URINAL

[75] Inventor: Masao Yamamoto, Tokyo, Japan

[73] Assignee: K. K. Musshu, Tokyo, Japan

[21] Appl. No.: 274,258

[22] Filed: Nov. 21, 1988

[30] Foreign Application Priority Data

Aug. 16, 1988 [JP] Japan .......................... 62-107850[U]

[51] Int. Cl.$^5$ .............................................. A47K 11/12
[52] U.S. Cl. ..................................... 4/144.2; 4/144.3; 604/368
[58] Field of Search .................... 4/144.1, 144.2, 144.3, 4/144.4, 450, 451, 454, 457, 458; 604/349, 329, 368, 350; 206/524.5, 634, 15, 438; 128/DIG. 24; 353/102; 422/117

[56] References Cited

U.S. PATENT DOCUMENTS

| | | | |
|---|---|---|---|
| 2,800,905 | 7/1957 | Simmons et al. | 128/DIG. 24 |
| 3,312,221 | 4/1967 | Overment | 604/350 |
| 3,890,974 | 6/1975 | Kozak | 604/368 |
| 3,952,741 | 4/1976 | Baker | 222/491 |
| 3,999,653 | 12/1976 | Haigh et al. | 206/524.5 |
| 4,188,304 | 2/1980 | Clarke et al. | 206/5 |
| 4,410,441 | 10/1983 | Davies et al. | 206/5 |
| 4,718,899 | 1/1988 | Itoh et al. | 604/368 |
| 4,795,032 | 1/1989 | Kandathil | 206/634 |

FOREIGN PATENT DOCUMENTS

| | | | |
|---|---|---|---|
| 2904634 | 8/1979 | Fed. Rep. of Germany | 604/368 |
| 6228240 | 5/1984 | Japan . | |
| 623144 | 1/1987 | Japan . | |
| 2188545 | 10/1987 | United Kingdom | 4/144.1 |

Primary Examiner—Charles E. Phillips
Attorney, Agent, or Firm—Fred Philpitt

[57] ABSTRACT

A portable urinal comprises: a urine-storage bag constructed of a waterproof material, the bag being provided with a mouth and a fastener, the mouth being so located as to cover the genitourinary area of a man or woman in use, the fastener being constructed of a grooved channel provided in the interior of a front-trunk portion of the bag at a suitable position thereof and a ridge which is provided in the interior of a rear-truck portion of the bag at a suitable position thereof while detachably inserted into the grooved channel in a snapping manner, both of the grooved channel and the ridge extending over a width of the bag; and a pouch, constructed of a water-permeable material, and filled with a water-absorbing agent which is swollen with urine to form a gel when brought into contact with the urine to absorb the same, the pouch being broken when the agent is swollen with urine.

1 Claim, 1 Drawing Sheet

PORTABLE URINAL

BACKGROUND OF THE INVENTION

1. Field of the Invention

The present invention relates to a portable urinal excellent in its ease of use for men and women, and more particularly to a portable urinal provided with a mouth element so located as to cover the genitourinary area of the user.

2. Description of the Prior Art

As is disclosed in Japanese Utility Model Publication No. 62-28240, a conventional portable urinal comprises a waterproof urine-storage bag provided with a pouch filled with powder of water-absorbing material, the pouch being constructed of water-soluble films. In such a conventional portable urinal, when the powder of the water-absorbing agent filled in the pouch is brought into contact with urine, the powder absorbs the urine to form a gel.

As described above, in the conventional portable urinal, since the pouches are constructed of water-soluble films, the conventional portable urinal suffers from the following disadvantages:

(a) since the films of the pouches are easily soluble in water, i.e., very sensitive to the moisture in the air, the moisture should be removed from the air as much as possible during the process of packaging the water-absorbing agent in the pouch. In case there is too much moisture in the air during the above process, the films of the pouches adhere to each other and/or to packaging machines to thereby lower the packaging efficiency of the process, which results in a poor yield of the product;

(b) a stock of the water-soluble film for the pouches must be stored in a dehumidifying room to prevent the films from being subjected to the moisture;

(c) a stock of the pouches filled with the water-absorbing agent also must be stored in the dehumidifying room to prevent the pouches from being subjected to the moisture; and (d) in shipping the product during the rainy season, the product must be double-packaged in a careful manner.

SUMMARY OF THE INVENTION

It is an object of the present invention to provide a novel portable urinal which is free from the above disadvantages inherent in the conventional portable urinal. The portable urinal of the present invention makes it possible to efficiently fill a pouch of the urinal with a water-absorbing agent, the pouch being made of a material which is not sensitive to the moisture to thereby promote packaging efficiency of the products and make it possible to eliminate expensive dehumidifying installations, which leads to a substantial cost reduction in installations.

According to the present invention, there are provided the following portable urinals (1) A portable urinal comprising:
a urine-storage bag constructed of a waterproof material; and
a pouch which is constructed of a water-permeable material that is filled with a water-absorbing agent which is swollen with urine to form a gel when it is brought into contact with said urine to absorb the same, said pouch being broken into fragments when said water-absorbing agent is swollen with said urine.

(2) A portable urinal comprising:
a urine-storage bag constructed of a waterproof material, said urine-storage bag being provided with a mouth element which is so located as to cover the genitourinary area of a man or woman in use; and
a pouch which is constructed of a water-permeable material that is filled with a water-absorbing agent which is swollen with urine to form a gel when it is brought into contact with said urine to absorb the same, said pouch being broken into fragments when said water-absorbing agent is swollen with said urine.

(3) A portable urinal comprising:
a urine-storage bag constructed of a waterproof material, said urine-storage bag being provided with: a mouth element which is so located as to cover the genitourinary area of a man or woman in use; and a fastener means constructed of a grooved channel means provided in the interior of a front portion of said urine-storage bag at a suitable position thereof and a ridge means which is provided in the interior of a rear portion of said urine-storage bag at a suitable position thereof while detachably inserted into said grooved channel means in a snap-fit manner, both said grooved channel means and said ridge means extending over the width of said urine-storage bag; and
a pouch which is constructed of a water-permeable material while filled with a water-absorbing agent which is swollen with urine to form a gel when brought into contact with said urine to absorb the same, said pouch being broken into fragments when said water-absorbing agent is swollen with said urine.

DESCRIPTION OF THE PREFERRED EMBODIMENTS

Figure 1:
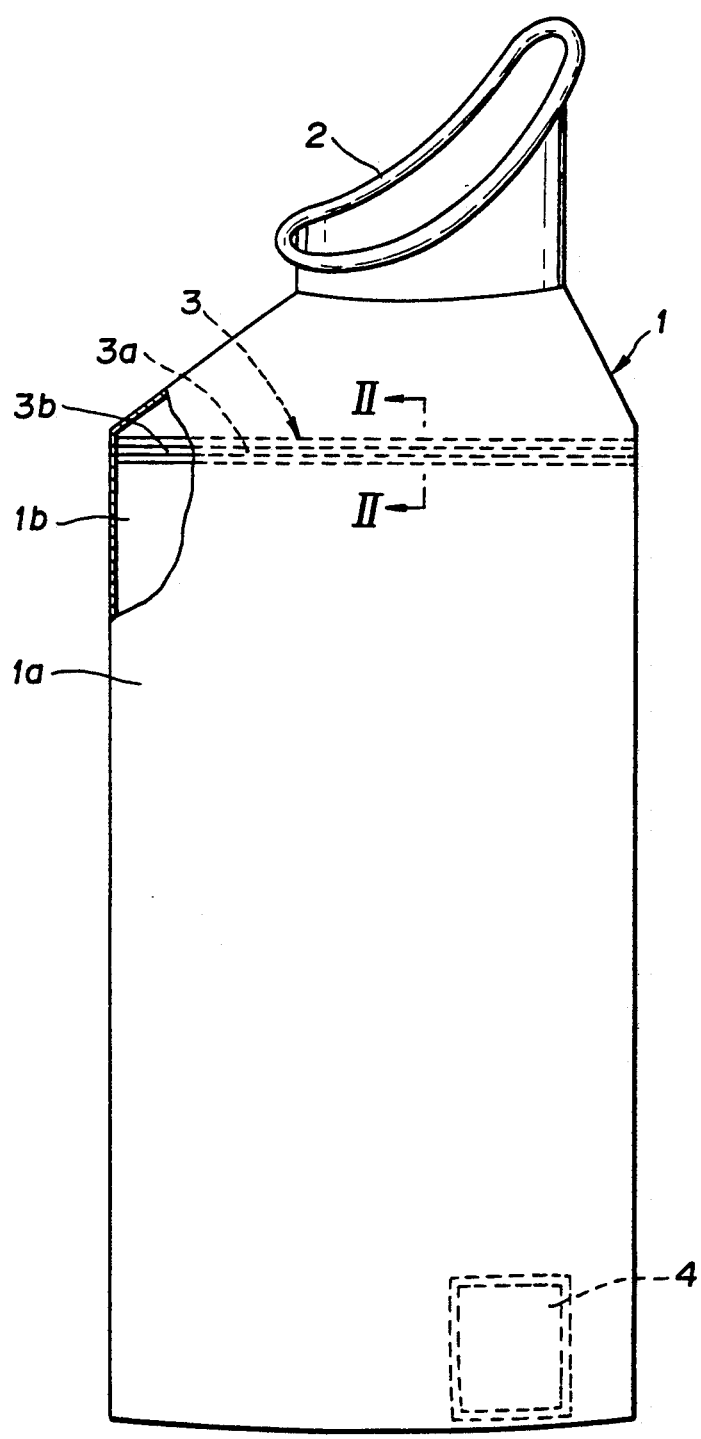
FIG. 1 is a partially broken front view of an embodiment of the portable urinal of the present invention.
Figure 2:
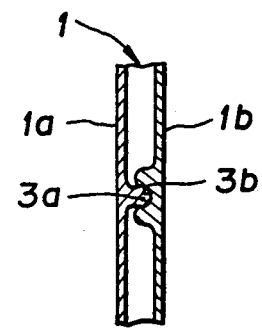
FIG. 2 is a cross-sectional view of the fastener means employed in the portable urinal of the present invention shown in FIG. 1, taken along the line 11—11 of FIG. 1.
Figure 3:
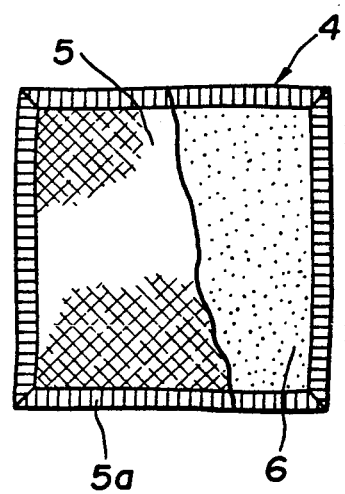
FIG 3 is a partially broken front view of the pouch filled with the water-absorbing agent employed in the portable urinal of the present invention shown in FIG. 1.

An embodiment of a portable urinal of the present invention will be hereinbelow described in detail with reference to the drawings, wherein: the reference numeral 1 denotes a urine-storage bag; 2 a mouth element of the urine-storage bag 1; 3 a fastener; 3a a ridge means of the fastener 3; 3b a grooved channel means of the to cooperate therewith; 4 a package for receiving a pouch 5 filled with the water-absorbing agent 6.

Construction of the Invention

As shown in FIG. 1, the urine-storage bag 1 is constructed of a suitable waterproof material such as synthetic resins and the like.

The urine-storage bag 1 is provided with a mouth element 2 in its upper portion. In use, such mouth element 2 of the urine-storage bag 1 is so located as to cover the genitourinary area of a man or woman in use. More particularly, in case of the woman, the mouth element 2 is located in the flush relation to her vulvovaginal area. The mouth element 2 of the urine-storage bag 1 may be made of a rigid or semi-rigid material so as to be foldable, if necessary. It is desirable that the mouth element 2 of the urine-storage bag 1 is appropriately harder than the remaining portion of the same 1.

In the interior of upper portions of a front-trunk portion 1a and a rear-trunk portion 1b of the urine-storage bag 1 are provided a pair of the ridge means 3a and the grooved channel means 3b which detachably receives the ridge means 3a therein in a snap-fit manner. Both of the ridge means 3a and the grooved channel means 3b horizontally extend around the circumference of the urine-storage bag 1 to form a fastener 3 for opening/closing the urine-storage bag 1 in its upper portion, as shown in FIG. 1.

In the package 4, powder of the water-absorbing agent 6 is filled in the pouch 5. When the water-absorbing agent 6 is brought into contact with urine, the agent 6 absorbs the urine so as to be swollen therewith, and finally forms a gel so as to coagulate the urine in the urine-storage bag 1.

At this time, when the water-absorbing agent 6 filled in the pouch 5 is swollen with the urine to form the gel, the pouch 5 is broken into fragments under the influence of an expansion pressure exerted by the gel thus formed in the pouch 5. Such breakage of the pouch 5 is intended to occur normally in a sealing-edge area 5a of the pouch 5.

Incidentally, a powder of acrylamide, its mixture with a powder of ammonium persulfate and the like may serve as the water-absorbing agent 6.

The water-permeable pouch 5 is constructed of a suitable material such as paper and cloth both treated with thermoplastic synthetic resins, non-woven fabric provided with a heat-sealability and like materials. In production, the pouch 5 is filled with the water-absorbing agent 6 and then heat-sealed at its peripheral portions such as the sealing-edge area 5a.

In use, the mouth element 2 of the urine-storage bag 1 provided with the package 4 of the pouch 5 filled with the water-absorbing agent 6 is so located as to cover the genitourinary area of the man and woman in use. In case of the woman, the mouth element 2 of the urine-storage bag 1 is located in flush relation to her vulvo-vaginal area.

When the urine is received in the urine-storage bag 1, some of the urine enters the water-permeable pouch 5 in the package 4, which pouch 5 has been filled with the water-absorbing agent 6. As a result, the water-absorbing agent 6 absorbs this urine, and is swollen with the same to form a gel. Under the influence of an expansion pressure exerted by the gel thus formed in the pouch 5, the pouch 5 is broken into fragments dispensing agent 6 so that all urine having been received in the urine-storage bag 1 is so coagulated as to become a gel.

After use, the urine-storage bag 1 is closed by means of the fastener 3, and, if necessary, then covered with a trash sack so as to be disposed.

Action of the Invention

In the portable urinal of the present invention, when the urine enters the urine-storage bag 1, the urine further enters the pouch 5 since the pouch 5 is permeable to water. As a result, the water-absorbing agent 6 filled in the pouch 5 is swollen with the urine to form a gel. The gel exerts its expansion pressure on the pouch 5 to break the same so that the water-absorbing agent contained in the pouch 5 is brought into a direct contact with the urine to coagulate it into a gel.

Effect of the Invention

The embodiment of the portable urinal of the present invention described above has the following advantages:

(a) since the urine received in the urine-storage bag 1 forms the gel in the bag 1, and since the bag 1 is closed by means of the fastener 3 after use, there is no danger that the urine received in the bag 1 will leak therefrom so that the portable urinal of the present invention is quite safe from leakage;

(b) since the urine-storage bag 1 is closed by means of the fastener 3 after use, there is no danger that a foul smell of the urine will emanate from the bag 1;

(c) since the material forming the pouch 5 of the package 4 filled with the water-absorbing agent 6 is not water-soluble, but merely permeable to water and therefore not sensitive to the moisture, the following advantages are derived therefrom:

(c1) in the packaging process of the water-absorbing agent 6, there is no need to remove the moisture from the air, which makes it possible to eliminate the dehumidifying installations so as to realize a minimum installation cost; and (c2) even when there is too much moisture in production line, there is no danger that the materials forming the pouch 5 will adhere to each other and/or to the packaging machines, which increase the yield of product.

In addition, the portable urinal of the present invention requires a minimum attention in its packaging and transportation operations with respect to the moisture in the air.

What is claimed is:

1. A portable urinal comprising:
a urine-storage bag constructed of a waterproof material, said urine-storage bag being provided at its top with a mouth element that can be located so as to cover the genitourinary area of a human body when in use; and a fastener located below said mouth and comprising a grooved channel provided along one half of the interior wall of said urine-storage bag and a mating ridge which is provided on the other half of the interior wall of said urine-storage bag, said ridge is adapted to engage said grooved channel in a snap-fit manner, both said grooved channel and said ridge extending across the entire width of said urine-storage bag so as to seal off said bag adjacent to said mouth element, and
a pouch positioned within said bag which is constructed of a water-permeable, water-insoluble material, said pouch being filled with a water-absorbing agent which when contacted with a portion of said urine in said bag will swell to form a gel, the wall strength of said pouch being such that the pouch will break into fragments when said water-absorbing agent becomes swollen with said urine, and thereby dispense said agent to the remainder of said urine in said bag to render a gel of the entire contents of said bag.

* * * * *